US00PP14479P29

(12) United States Plant Patent
Zaiger et al.

(10) Patent No.: US PP14,479 P2
(45) Date of Patent: Jan. 20, 2004

(54) PEACH TREE NAMED 'SNOW PEAK'

(50) Latin Name: *Prunus persica*
Varietal Denomination: Snow Peak

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/402,799

(22) Filed: Mar. 31, 2003

(51) Int. Cl.[7] ..... A01H 5/00
(52) U.S. Cl. ..... Plt./195
(58) Field of Search ..... Plt./195

*Primary Examiner*—Anne Marie Grunberg

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices such as pruning, thinning, spraying, irrigation and fertilization. Its novelty consist of the following combination of desirable features:

1. Vigorous, upright growth.
2. Heavy and regular production of medium size fruit.
3. Fruit having an attractive red skin color.
4. Fruit with very good flavor and eating quality.
5. Fruit with mild, sweet, sub-acid, white flesh.
6. Fruit that ripens in the early maturity season.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of nectarine and peaches, which are known to us, and mentioned herein, 'Ruby Gold' Nectarine (U.S. Plant Pat. No. 3,101), 'Red Wing' Peach (U.S. Plant Pat. No. 621), 'Starlite' Peach (non-patented), 'Sugar Lady' Peach (U.S. Plant Pat. No. 7,532), 'Desert Gold' Peach (non-patented) and 'May Crest' Peach (U.S. Plant Pat. No. 4,064).

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard as a first generation seedling from seed collected from a cross between proprietary lines of immediate parents with field identification numbers 9GG32 and 2LD470. The maternal parent (9GG32) originated from crosses between the following varieties; 'Ruby Gold' Nectarine (U.S. Plant Pat. No. 3,101), 'Red Wing' Peach (U.S. Plant Pat. No. 621) and 'Starlite' Peach (non-patented). The paternal parent (2LD470) originated from crosses between the following varieties; 'Red Wing' Peach (U.S. Plant Pat. No. 621), 'Sugar Lady' Peach (U.S. Plant Pat. No. 7,532), 'Desert Gold' Peach (non-patented) and 'May Crest' Peach (U.S. Plant Pat. No. 4,064) We planted and grew a large number of these first generation seedlings on their own root system. We also budded each of these seedlings to previously planted 'Nemaguard' Rootstock (non-patented) to induce earlier fruit maturity. Under close and careful observation we recognized the desirable fruit characteristics of the present variety and selected it for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new peach tree (*Prunus persica*) is of large size, vigorous, upright growth and a productive and regular bearer of medium size, white flesh, clingstone fruit, with very good flavor and eating quality. The fruit is further characterized by ripening in the early maturity season, having a high degree of attractive red skin color, firm, white flesh with good handling and shipping quality. In comparison to 'May Crest' Peach (U.S. Plant Pat. No. 4,064), the flesh of the new variety is white instead of yellow, is sub-acid instead of acidic and is approximately 2 days earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large. Pruned to 3 to 3.5 meters in height at maturity for economical harvesting of fruit.

*Vigor.*—Vigorous. Growth of 1.5 to 2 meters the first growing season. Varies with soil fertility and cultural practices.

*Form.*—Upright. Usually pruned to vase shape.

*Branching habit.*—Upright. Crotch angle approximately 35°. Heavy fruit production increases crotch angle.

*Productivity.*—Productive. Usually sets 1½ or more times the amount of fruit desired, thinning and spacing are necessary to develop market size fruit.

*Bearer.*—Regular. Has had heavy production 3 consecutive years.

*Fertility.*—Self-fertile.

*Density.*—Medium dense. Pruning to vase shape by removing branches and foliage from center of tree to increase sunlight and air movement throughout tree.

*Hardiness.*—Hardy in all stone fruit growing areas in California. Trees growing in USDA Hardiness Zone 9. Winter chilling requirement of approximately 300 hours at or below 45° F.

Trunk:

*Size.*—Large. Average circumference 45.7 cm at 30.5 cm above ground.

*Stocky.*—Medium stocky.

*Texture.*—Medium rough, becomes rougher with age.

*Color.*—Varies from 10YR 5/2 to 10YR 6/2, color darkens with age.

Branches:

*Size.*—Medium. Average circumference 20.3 cm at 1.5 meters above ground.

*Surface texture.*—Smooth on new growth. Mature growth medium rough.

*Lenticels.*—Average number of 46 in a 25.8 square cm section. Average length 2.8 mm. Average width 1.3 mm. Color varies from 5YR 4/4 to 5YR 4/6, varies with age of growth.

*Color.*—New growth varies from 2.5R 3/8 to 2.5R 5/8 in areas exposed to sun, 2.5GY 7/6 to 7.5GY 6/8 in shaded areas. Old growth from 2.5Y 5/2 to 2.5Y 5/4, varies with age of growth.

Leaves:

*Size.*—Large. Average length 129.1 mm. Average width 34.0 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentation over midrib and leaf veins, glabrous. Lower surface relatively smooth, small ridges created by midrib and pinnate venation, glabrous.

*Petiole.*—Average length 9.9 mm. Average width 1.6 mm. Longitudinally grooved. Glabrous. Color varies from 2.5GY 6/6 to 5GY 6/6.

*Glands.*—Reniform. Medium size. Average length 1.0 mm. Average width 0.5 mm. Number varies from 2 to 4, average number 2. Located on the base of the leaf blade and the upper portion of the petiole. Color varies from 2.5GY 6/6 to 5GY 6/6.

*Color.*—Upper surface varies from 2.5GY 4/4 to 5GY 4/6. Lower surface varies from 2.5GY 5/6 to 5GY 5/4. Midvein color varies from 2.5GY 8/4 to 5GY 8/4.

Flower buds:

*Size.*—Large. Average length 18.8 mm. Average diameter 10.6 mm.

*Hardiness.*—Hardy in all stone fruit growing areas of California.

*Form.*—Plump, conical, becoming elongated before opening.

*Pedicel.*—Average length 4.8 mm. Average width 1.2 mm. Color 2.5GY 6/8.

*Color.*— 5RP 7/6.

Flowers:

*Size.*—Large, showy. Average height 21.8 mm. Average diameter 35.4 mm.

*Petals.*—Number 5, alternately arranged to sepals. Shape — orbicular. Average length 18.1 mm. Average width 15.0 mm. Margin varies from entire to sinuate. Color ranges from 2.5RP 7/6 to 2.5RP 8/6.

*Sepals.*—Number 5, alternately arranged to petals. Shape — oblong, apex rounded. Pubescence — inner surface glabrous, outer surface pubescent. Average length 5.9 mm. Average width 4.0 mm. Color — inner surface 7.5RP 4/10 mixed with 2.5GY 5/8. Outer surface 7.5RP 4/6.

*Stamens.*—Average number per flower 45. Average filament length 13.0 mm. Filament color N 9.5/ when flower first opens, becoming 2.5RP 6/8 as flower ages. Anther color 6.25R 5/12.

*Pollen.*—Present, self-fertile. Color 2.5Y 8.5/8.

*Pistil.*—Normally 1, varies from 1 to 2. Average length 19.1 mm. Surface is pubescent. Color 7.5Y 9/4. Stigma approximately 1.1 mm lower than anthers.

*Fragrance.*—Very slight.

*Blooming period.*—Date of First Bloom Feb. 19, 2002. Date of Petal Fall Mar. 3, 2002. Varies slightly with climatic conditions.

*Color.*—Ranges from 2.5RP 7/6 to 2.5RP 8/6.

*Number flowers per flower bud.*—One.

*Pedicel.*—Average length 5.9 mm. Average width 1.2 mm. Color 2.5GY 7/10.

Fruit:

*Maturity when described.*—Firm ripe.

*Date of first picking.*—May 17, 2002.

*Date of last picking.*—May 24, 2002, varies slightly with climatic conditions.

*Size.*—Medium. Average diameter axially 61.0 mm. Average transversely in suture plane 66.5 mm. Average weight 153.4 grams, average weight varies slightly with fertility of the soil, amount of thinning and climatic conditions.

*Form.*—Globose, some fruit with slight pistil point.

*Suture.*—Nearly smooth, extends from base to apex.

*Ventral surface.*—Nearly rounded, only slightly lipped.

*Apex.*—Usually rounded, varies from rounded to slight pistil point.

*Base.*—Flat to slightly retuse.

*Cavity.*—Rounded to slightly elongated in suture plane. Average depth 8.4 mm. Avergae diameter 13.7 mm.

Stem:

*Size.*—Average length 8.9 mm. Average diameter 3.2 mm.

*Color.*—Varies from 2.5GY 7/8 to 2.5GY 7/10.

Flesh:

*Ripens.*—Evenly to slightly earlier at apex.

*Texture.*—Firm, meaty.

*Fibers.*—Few, small, tender.

*Firmness.*—Firm, comparable to 'May Crest' Peach (U.S. Plant Pat. No. 4,064).

*Aroma.*—Moderate.

*Amydgalin.*—Undetected.

*Eating quality.*—Very good.

*Flavor.*—Very good, mild, sweet, sub-acid.

*Juice.*—Moderate amount, enhances flavor.

*Brix.*—Average 9.8°, varies slightly with amount of fruit per tree and climatic conditions.

*Color.*—Varies from 5Y 9/2 to 5Y 8.5/2. Pit cavity varies from 5Y 8/4 to 5Y 8.5/4, non-bleeding.

Skin:

*Thickness.*—Medium.

*Surface.*—Smooth.

*Pubescence.*—Pubescent, moderate amount. Relatively short.

*Tendency to crack.*—None.

*Color.*—Ground color varies from 5Y 9/4 to 7.5Y 8.5/4. Nearly overspread with 5R 3/10 to 5R 4/10. Random areas of ground color partially exposed creating a mottling pattern to skin surface.

*Tenacity.*—Tenacious to flesh.

*Astringency.*—Undetected.

Stone:

*Type.*—Clingstone.

*Size.*—Medium. Average length 27.8 mm. Average width 21.7 mm. Average thickness 16.3 mm.

*Form.*—Ovoid.

*Base.*—Varies from straight to rounded.

*Apex.*—Cuspidate. Average length 2.7 mm.

*Surface.*—Irregularly furrowed toward the apex, pitted toward base. Pits vary from round to elongated. Usually one furrow on each side of suture.

*Sides.*—Vary from equal to unequal, with one side extending further from suture plane.

*Ridges.*—Medium width, relatively smooth.

*Tendency to split.*—Slight.

*Color.*—Varies from 7.5YR 7/6 to 10YR 7/8 when dry.

Kernal:

*Form.*—Elliptic.

*Taste.*—Bitter.

*Viability.*—Non-viable, incomplete embryo.

*Size.*—Average length 16.7 mm. Average width 11.1 mm. Average thickness 5.3 mm.

*Skin color.*—Varies from 2.5Y 9/2 to 5Y 9/2.

Use:

*Dessert.*—Market — local and long distance.

Keeping quality: Good, held firm in cold storage 3 weeks at 38 to 42° F. with minimal loss of flavor, firmness or internal flesh breakdown.

Shipping quality: Good, minimal bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

Claim:

1. A new and distinct variety of peach tree, substantially as illustrated and described, characterized by its large size, vigorous upright growth and being a productive and regular bearer of medium size, white flesh fruit that ripen in the early maturity season, with sweet, sub-acid flesh that has very good flavor and eating quality; the fruit is further characterized by its attractive red skin color, its good handling and shipping quality and, in comparison to 'May Crest' Peach (U.S. Plant Pat. No. 4,064) the flesh is white instead of yellow, it is sub-acid instead of acidic and ripens approximately 2 days earlier.

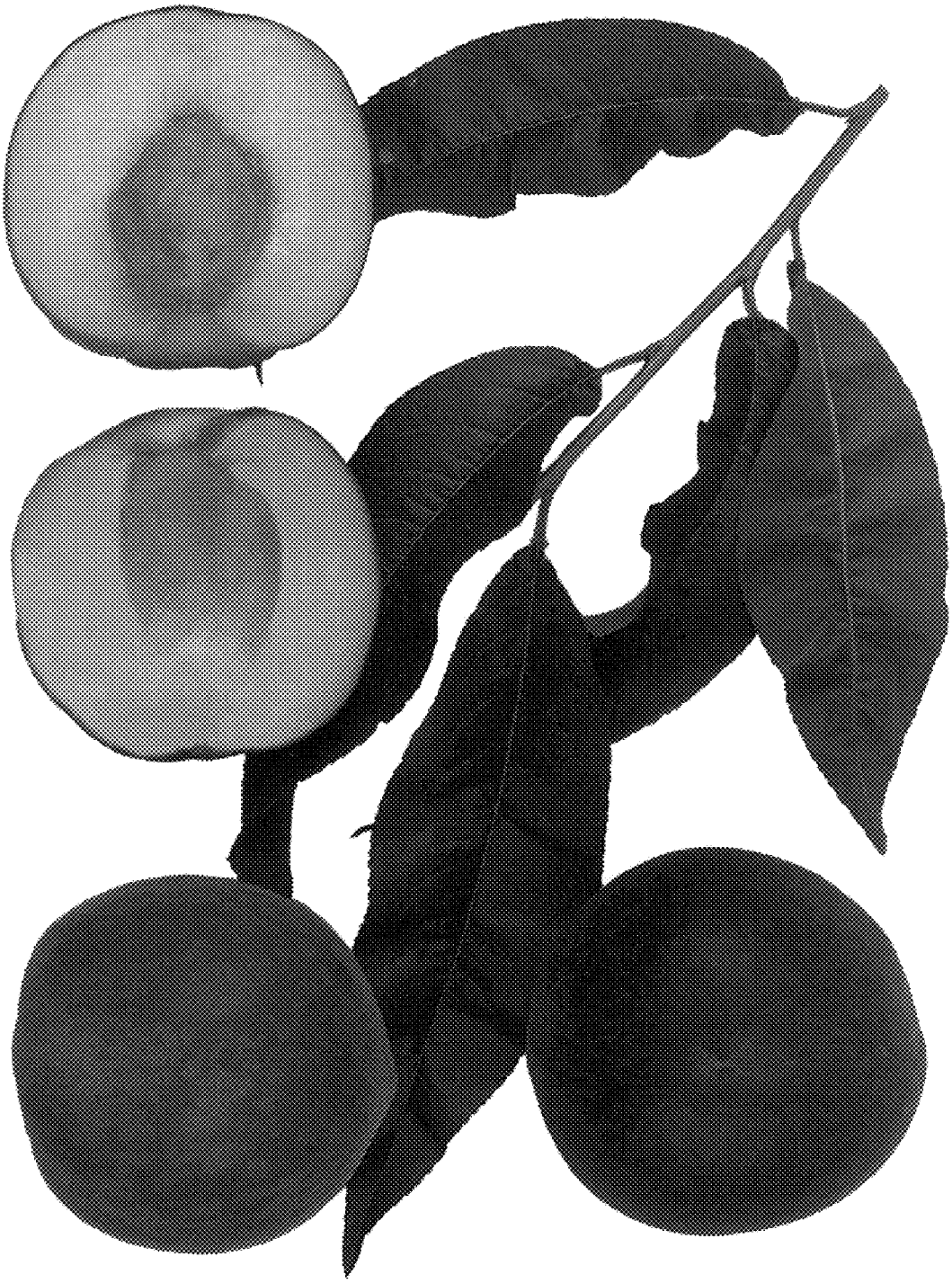

* * * * *